United States Patent [19]

Qu

[11] Patent Number: 4,600,026

[45] Date of Patent: Jul. 15, 1986

[54] TOBACCO COMPOSITION WITH BLUISH DOGBANE AND A PROCESS FOR THE PREPARATION THEREOF

[76] Inventor: Dong-Fen Qu, c/o Beijing Cigarettes Factory, Beijing, China

[21] Appl. No.: 711,620

[22] Filed: Mar. 14, 1985

[51] Int. Cl.⁴ ..................... A24B 15/16; A24B 15/28; A24D 1/18
[52] U.S. Cl. .................................... 131/335; 131/331; 131/309; 131/310; 131/359
[58] Field of Search ............... 131/331, 359, 335, 309, 131/310

[56] References Cited

PUBLICATIONS

Alien Propert Custodian Ser. No. 261,049 Jules Lande.

*Primary Examiner*—V. Millin
*Attorney, Agent, or Firm*—Morgan, Finnegan, Pine, Foley & Lee

[57] ABSTRACT

The present invention relates to a tobacco composition comprising tobacco and bluish dogbane in the form of bluish dogbane leaves or bluish dogbane extract, a process for making the tobacco composition and a process for producing bluish dogbane extract. The tobacco composition of the present invention is useful to alleviate and cure chronic bronchitis caused by smoking.

24 Claims, No Drawings

TOBACCO COMPOSITION WITH BLUISH DOGBANE AND A PROCESS FOR THE PREPARATION THEREOF

INTRODUCTION

This invention relates to a tobacco composition comprising tobacco and bluish dogbane, apocynum venetum, and a process for making the tobacco composition. More particularly, it relates to a novel tobacco composition containing bluish dogbane extract or bluish dogbane leaves. The novel tobacco composition is useful for alleviating chronic bronchitis, reducing phlegm, relieving cough, and improving the condition of the lungs.

BACKGROUND OF THE INVENTION

Since the discovery that smoking is harmful to health, there has been a world wide effort by the tobacco industry to research and develop a safe non-toxic tobacco composition. It is hoped that a tobacco composition can be developed to alleviate or even to prevent cancer, coronary heart disease, and other pulmonary diseases caused by smoking.

Up to the present, processes for improving the tobacco combustion process to reduce the content of tar, nicotine and carbon monoxide in tobacco smoke have been developed. These include the production of cigarets with improved ventilation, cigarets with synthetic low tar tobacco, a process to fluff tobacco, as well as putting additives in tobacco compositions.

Many additives for tobacco has been reported. Most of the additives used are chemicals, such as metal palladium and its salts, nitrates, silicates, sugar, etc. See U.S. Pat. Nos. 3,338,246; 2,429,567; 4,248,251 and German patent application No. 817,717. These additives are found to be somewhat useful in improving the combustion process to reduce tar, nicotine and carbon monoxide content in tobacco smoke.

Among diseases induced by smoking, chronic bronchitis claims the highest number of victims. About 50-80% chronic bronchitis patients are smokers. Chronic bronchitis caused by smoking is therefore, a major health hazard. However, up to the present, very few studies has been undertaken to relieve this condition and no successful effort has been reported.

It is, therefore, an objective of the present invention to develop a tobacco composition which is effective in easing chronic bronchitis, reducing phlegm, relieving coughing, and improving the condition of the lung. It is a further objective of the present invention to develop an easy and inexpensive process to produce a tobacco composition with low tar, and nicotine content.

SUMMARY OF THE INVENTION

According to the present invention, a tobacco composition containing an effective amount of bluish dogbane, its leaves or an extract thereof, a process for producing the tobacco composition and a process for producing bluish dogbane extract have been developed. The presence of bluish dogbane in tobacco composition buffers and offsets the tar, nicotine and carbon monoxide contents of the tobacco smoke.

The tobacco composition comprises:
(a) dry tobacco leaves; and
(b) an effective amount of bluish dogbane in the form of fermented bluish dogbane leaves or an extract of bluish dogbane.

The present invention further provides a process for preparing bluish dogbane extract and a process for making a tobacco composition with bluish dogbane.

The process for making bluish dogbane extract comprises:

(a) steam cooking bluish dogbane leaves in a polar solvent, selected from the group comprising water and alcohol with constant agitation for from about 0.5 to 4 hours;

(b) filtering the cooked mixture to remove solid residue; and (c) vacuum drying the filtrate at a temperature up to about 80° C.

The process for making a tobacco composition containing bluish dogbane comprises mixing tobacco, tobacco additives with an effective amount of bluish dogbane in the form of bluish dogbane leaves or bluish dogbane extract.

DETAILED DESCRIPTION OF THE INVENTION

In accordance with the present invention bluish dogbane extract or bluish dogbane leaves can be mixed with tobacco to make cigarets, cigars, pipe tobacco or chewing tobacco. The presence of bluish dogbane in the tobacco composition affect the upper respiratory tract and is useful to alleviate chronic bronchitis.

Bluish dogbane is a herbal medicine known in China. According to chemical analysis, it contains various components such as quercetin, sterols, anthraguinone, amino acids, etc. It is non-toxic. See Chinese Pharmacopoeia (1977). The chemical structure of quercetin in bluish dogbane has been determined to be 3,5,7,3',4'-quinque-hydroxy-flavone. It is known to be useful for reducing phlegm and relieving coughs.

The tobacco composition of the present invention may be prepared according to the following methods.

Tobacco useful for producing cigarets, cigars, pipe tobacco or chewing tobacco is mixed with a small amount of conventional tobacco additives and fermented bluish dogbane leaves. The amount of bluish dogbane leaves is at least 1% by weight, from about 1% to 50% by weight, of the total dry weight of the tobacco composition.

For making cigarets and pipe tobacco, the amount of fermented bluish dogbane leaves is preferably 15%–40% by weight of the tobacco composition. However, for best aroma and medical effectiveness, most preferably, the amount of fermented bluish dogbane leaves is from about 15 to 25% by weight of the tobacco composition.

For making cigars, the amount of fermented bluish dogbane leaves is preferably 25 to 35% of the total weight of the mixture.

In the alternative, tobacco may be mixed with a small amount of common tobacco additives and an extract of bluish dogbane. The extract can be prepared by using polar solvents selected from the group comprising water and alcohol. The extract is concentrated and dried. It has been found that about 1 g of dried extract is as effective as 10 g of dry bluish dogbane leaves. The extract can be used either in dry form or in an aqueous solution. The effective level of the extract in the tobacco composition is at least 0.1% by weight, about 0.1–10% by weight, based the total dry weight of the composition.

For making cigarets or pipe tobacco, the amount of bluish dogbane extract is about 0.5–4% by weight, preferably about 0.5–1.5% by weight, based on the total dry weight of the composition. When the process is adopted for making cigars, the amount of bluish dogbane extract is about 0.5–4% by weight, and preferably 2–4% by weight of the total dry weight of the tobacco composition. When the amount of the extract is below 4% of the total dry weight of tobacco composition, the tobacco composition does not present any unpleasant aroma and is medically effective.

The preferred solvent for the preparation of the extract is water, because water does not create environmental pollution. Further, water is not toxic, which means that any water remaining in the tobacco composition need not be removed.

Clean bluish dogbane plant or leaves are placed in a container with an agitator and a sufficient amount of water, about ten times as much by volume of water, is added. The mixture is cooked for about 0.5–4 hours either with a heater, or by direct injection of steam. Solids are removed by filtration. The filtrate is concentrated under vacuum at a temperature below 80° C., and then dried. It is important that the temperature used for drying should not be over 80° C. Otherwise, the bluish dogbane extract will carbonize and be deactivated. Usually, the amount of extract obtained is about 1/10 by weight of the bluish dogbane leaves used.

The extract thus made is brown, has a slightly puckery taste, and contains about 0.1–1.5% by weight of quercetin. If the extract is mixed with hot water in a ratio of 1:20, at 80° C., the extract will completely dissolve.

Bluish dogbane extract produced by using polar solvents can be mixed with tobacco either in dry form or as an agueous solution to produce cigarets, cigars, pipe tobacco and chewing tobacco.

Bluish dogbane extract, conventional tobacco additives and sufficient water are mixed. The mixture is boiled and agitated for about 5 minutes to 1 hour. The mixture is cooled to 45°–60° C., and filtered. The filtrate is spread on warm and moistened tobacco leaves. The treated tobacco leaves is kept at about 25°–35° C. under about 60–75% relative humidity for about 2–48 hours. The tobacco leaves can then be further processed into cigarets, cigars, pipe tobacco or chewing tobacco. The amount of bluish dogbane extract used is in the range from about 0.1 to 10%, preferably from about 0.5% to 4% depending on the type of tobacco product desired.

The following examples illustrates the present invention.

EXAMPLE 1

Preparation of Bluish Dogbane Water Extract 100 kg of bluish dogbane leaves were placed in a reactor with an agitator, 1000 kg water were added and, agitated for two hours with gentle boiling. After cooling 830 kg of filtrate was collected by vacuum filtration. The filtrate was concentrated at 80° C. and reduced pressure, 18 kg of concentrate was produced. The concentrate was dried for one hour under vacuum at 80° C. 10 kg of bluish dogbane water extract were collected.

The characteristics of the extract were as follows:
Color: brown;
taste: slightly puckery;
quercetin content: 0.98%, as flavone
Solubility: dry bluish dogbane extract was mixed with hot water at 80° C. in the ratio of 1:20, and dissolved completely.

EXAMPLE 2

Preparation of Tobacco Composition Comprising 0.5% Bluish Dogbane Water Extract 49.1 kg of evenly mixed tobacco leaves, were placed in a conditioning cylinder. The tobacco leaves were fluffed and conditioned with circulating hot and moist air at a temperature of 50° C.

0.25 kg of dry bluish dogbane water extract, produced as described in Example 1, was placed in a small container. 0.5 kg glucose, 0.25 kg extract of glycyrrhiza and 0.125 kg white wine, made from grains such as rice, wheat, rye, sorghum, and sufficient amount of water were added. The mixture was gently boiled, filtered and cooled to 50° C.

The solution was sprayed through steam nozzles onto the surface of the conditioned tobacco leaves to raise the moisture content of the tobacco leaves to about 20%. The tobacco leaves were for then stored 4 hours at 30° C. under 70% relative humidity. The treated tobacco leaves were then made into cigarets, and pipe tobacco.

EXAMPLE 3

Preparation of Tobacco Composition Comprising 4% Bluish Dogbane Water Extract

After thrashing to separate the stems, 46.4 kg of evenly mixed tobacco leaves were subjected to conditioning and casing. The tobacco leaves were loosened in the conditioning cylinder and hot moist air was circulated into the conditioning cylinder to raise the temperature of the tobacco leaves to 60° C.

2 kg of dry bluish dogbane water extract, prepared in accordance to the method described in Example 1, was placed in a small container. 1 kg of glucose, 0.1 kg of extract of glycyrrhiza, 0.25 kg of tincture of dates, 0.25 kg of white grain wine and water were added and mixed. The mixture was gently boiled, filtered and cooled to 60° C.

The filtrate was mixed with compressed air and sprayed onto the surface of the conditioned tobacco leaves to bring the moisture level to 18%. The treated tobacco leaves were kept at 35° C. under a relative humidity of 80% for 8 hours. After which the treated tobacco leaves were made into cigarets or cigars.

EXAMPLE 4

Preparation of Tobacco Composition Comprising 1% of Bluish Dogbane Water Extract 12 kg of tobacco stems were placed into a steamer extruder for high temperature and high moisture treatment. 0.15 kg powdered dry bluish dogbane water extract were added. After treatment, the moisture content of the tobacco stems should be 28% and at a temperature of 75° C. The treated stems were cooled and stored fo 6 hours.

0.35 kg of dry bluish dogbane water extract were placed in a small container. 1 kg of glucose, 0.05 kg of extract of glycyrrhiza and 0.25 kg white grain wine were added and mixed by stirring. An appropriate amount of water was added. The mixture was slightly boiled, filtered and cooled to 50° C. The filtrate was sprayed onto the surface of 36.2 kg tobacco leaves which had been conditioned in accordance with the method described in Example 2.

The tobacco leaves and stems were mixed and stored for 4 hours and then made into cigarets, cigars and pipe tobacco.

EXAMPLE 5

Preparation of Tobacco Composition Comprising 20% Bluish Dogbane Leaves 40 kg of evenly mixed tobacco leaves were shredded into stock more than 80% of which were about 12.5 mm in size. The shredded stock was mixed with 10 kg fermented bluish dogbane leaves on a mixing belt. The mixture was treated by conditioning according to conventional procedures and made into cigarets, cigars and pipe tobacco.

EXAMPLE 6

Preparation of Tobacco Composition Comprising 30% Bluish Dogbane Leaves 35 kg of evenly mixed tobacco leaves were shredded to make a stock comprising more than 80% of tobacco leave fractions of about 12.5 mm in size. This was mixed evenly with 15 kg fermented bluish dogbane leaves on a mixing belt. The mixture was treated by conditioning in accordance to conventional procedures and made into cigars and pipe tobacco.

EXAMPLE 7

A tobacco composition prepared from bluish dogbane leaves and tobacco according to the present invention were made into cigarets and given to 100 patients with chronic bronchitis caused by smoking. The patients smoke cigarets containing 40% bluish dogbane leaves and 60% tobacco for 15 consecutive days, at the rate of 20 cigarets a day each 2 cigarets each time. Then the patients were given cigarets containing 20% bluish dogbane leaves and 80% tobacco for another 30 days at the rate of 20 cigarets a day each. The results are shown in the table below:

| Number of Patients Treated | Cured | Improved | With No Effect | Effectiveness |
| --- | --- | --- | --- | --- |
| 100 | 42 | 40 | 18 | 82% |

EXAMPLE 8

A tobacco composition of bluish dogbane leaves and tobacco were made into cigars and given to 106 chronic bronchitis patients for treatment. The patients smoked cigars containing 30% bluish dogbane leaves and 70% tobacco for 30 days, at the rate of 5 cigars for each patient each day and half a cigar each time. Each cigar is approximately twice the size of a cigaret. The results are shown in the table below:

| Number of Patients Treated | Cured | Improved | With No Effect | Total Effectiveness |
| --- | --- | --- | --- | --- |
| 106 | 34 | 67 | 5 | 95.3% |

EXAMPLE 9

A tobacco composition comprising 1% bluish dogbane water extract based on the total dry weight of the tobacco composition, was made into cigarets and given to 43 chronic bronchitis patients. The trial lasted for 60 days in total, with 10–20 cigarets for each patient each day. The clinical effects are shown in the table below:

| Clinically Stabilized | Cured | Improved | With No Effect | Effectiveness |
| --- | --- | --- | --- | --- |
| 5 | 23 | 12 | 3 | 93.0% |

The medical effects analysis and bronchitis diagnosis were all carried out in accordance with "Chinese Criteria for Chronic Bronchitis Diagnosis Classification and Judgement of Medical Effects".

The tobacco composition, of the present invention was tested and showed the following additional effects:

1. Cigarets made of tobacco composition comprising 1% bluish dogbane extract produce 15% less carbon monoxide than those without bluish dogbane.

2. Toxicity ($LD_{50}$) on mice was obtained by using cigaret smoke from a tobacco composition comprising 1.5% bluish dogbane extract. The result was compared with toxicity on mice subjected to normal cigaret smoke. The results indicated that the toxicity ($LD_{50}$) of cigarets with bluish dogbane cigarets is 23% lower than conventional cigarets.

3. Smoking bluish dogbane cigarettes has less adverse effect on the performance of lungs than smoking conventional cigarets. The rate of annual progressive increase in the ratio of residual air to the lung's total capacity, was found to be 25%. The vital capacity of the lung of bluish dogbane cigarets smokers were found to be the same as that of non smokers. This indicates that the bluish dogbane cigarets are much safer than conventional cigarets.

Experiments also showed that bluish dogbane extract contains quercetin, in an amount about 0.1–1.5% by weight flavone. Queroetin was shown to be effective in reducing phlegm and relieving coughing.

What is claimed is:

1. A tobacco composition for alleviating chronic bronchitis comprising:
   (a) tobacco; and
   (b) bluish dogbane extract in an amount of at least 0.1% by weight based on the total dry weight tobacco composition.

2. A tobacco composition according to claim 1 wherein the amount of bluish dogbane extract is between about 0.1 and 10% by weight of the tobacco composition.

3. A tobacco composition according to claim 2 wherein the amount of bluish dogbane extract is between about 0.5 and 4% by weight of the total dry weight of the tobacco composition.

4. A tobacco composition according to claim 3 for use in cigarets or pipe tobacco wherein the amount of bluish dogbane extract is between about 0.5 and 1.5% by weight of the total dry weight of the tobacco composition.

5. The tobacco composition according to claim 3 for use as cigars wherein the amount of bluish dogbane extract is between about 2 and 4% by weight of the total dry weight of the tobacco composition.

6. The tobacco composition according to claim 1 wherein bluish dogbane extract is dissolved in water.

7. A tobacco composition according to claim 1 wherein bluish dogbane extract contains 0.1 to 1.5% quercetin by weight of the weight of the bluish dogbane extract.

8. A tobacco composition for alleviating chronic bronchitis comprising:
    (a) tobacco;
    (b) bluish dogbane leaves, in an amount of at least 1 percent by weight of the total dry weight of tobacco composition.

9. A tobacco composition according to claim 8 wherein the amount of bluish dogbane leaves is between about 1 and 50% by weight of the total dry weight of the tobacco composition.

10. The tobacco composition of claim 9 for use in cigarets or pipe tobacco wherein the amount of bluish dogbane leaves is between about 15 and 25% by weight of the total dry weight of the tobacco composition.

11. The tobacco composition of claim 9 for use in cigars wherein the amount of bluish dogbane leaves is between about 25 and 35% by weight of the total dry weight of the tobacco composition.

12. The process for preparing bluish dogbane extract for use in tobacco composition for alleviate chronic bronchitis comprising:
    (a) boiling the bluish dogbane with water, in an amount about 10 times the volume of bluish dogbane, in a container;
    (b) filtering the boiled extract;
    (c) concentrating and drying the filtrate under vacuum at a temperature below 80° C.

13. The process of claim 12 wherein the bluish dogbane is boiled with water for about 0.5 to 4 hours.

14. The process of claim 12 wherein the filtrate is vacuum dried at 80° C.

15. A process for preparing a tobacco composition containing bluish dogbane extract for alleviating chronic bronchitis comprising the steps of:
    (a) boiling with stirring bluish dogbane extract, other common tobacco additives and sufficient amount extract of a polar solvent selected from the group comprising water and alcohol in a container;
    (b) cooling and filtering the mixture; and
    (c) spreading the filtrate on the warm and moistened surfaces of tobacco leaves.

16. The process of claim 15 wherein the amount of bluish dogbane extract is at least 0.1% by weight of the total dry weight of the tobacco composition.

17. A process of claim 16 wherein the amount of bluish dogbane extract is between about 0.1 and 10% by weight of the total dry weight of the tobacco composition.

18. The process of claim 15 wherein the amount of bluish dogbane extract is between about 0.5 and 4 percent by weight of the total dry weight of the tobacco composition.

19. The process of claim 15 wherein the polar solvent is water.

20. A process for preparing a tobacco composition containing bluish dogbane for alleviating chronic bronchitis comprising the steps of:
    (a) mixing tobacco evenly with fermented bluish dogbane leaves in amount of about 1% to 50% by weight of bluish dogbane leaves based on the total dry weight of the composition; and
    (b) conditioning the mixture in hot moist air at a temperature in the range of about 40° C. to 70° C.

21. A process according to claim 20 wherein the amount of bluish dogbane leaves is about 15% to 25%.

22. A process according to claim 21 wherein the amount of bluish dogbane leaves is about 25% to 35%.

23. A tobacco composition for alleviating chronic bronchitis comprising:
    (a) tobacco and
    (b) an effective amount of quercetin.

24. A tobacco composition according to claim 23 wherein quercetin is present in an amount of about 0.0001% to 0.0015% by weight of the total dry weight of the composition.

* * * * *